United States Patent [19]

Zaffran et al.

[11] 4,318,297
[45] Mar. 9, 1982

[54] PENDULUM-TYPE FILM HARDNESS MEASUREMENT TESTER

[75] Inventors: Christian Zaffran, Elancourt; Jean-Claude Ser, Beynes; Jean-Pierre Yquel, Colombes, all of France

[73] Assignee: L'Oreal, Paris, France

[21] Appl. No.: 38,634

[22] PCT Filed: Nov. 23, 1978

[86] PCT No.: PCT/FR78/00042
§ 371 Date: May 14, 1979
§ 102(e) Date: May 14, 1979

[87] PCT Pub. No.: WO79/00322
PCT Pub. Date: Jun. 14, 1979

[30] Foreign Application Priority Data

Nov. 25, 1977 [FR] France ................ 77 35500

[51] Int. Cl.³ .................................................. G01N 3/50
[52] U.S. Cl. .................................................. 73/78
[58] Field of Search ................................. 73/78, 150 R

[56] References Cited

U.S. PATENT DOCUMENTS 2,757,535  8/1956  Monk ......................... 73/78
2,890,585  6/1959  Albrecht ..................... 73/150

FOREIGN PATENT DOCUMENTS 2347673 11/1977 France ........................... 73/78
1165276  9/1969 United Kingdom ............ 73/78

Primary Examiner—James J. Gill
Attorney, Agent, or Firm—N. Jerome Rudy

[57] ABSTRACT

A novel automatic test measuring apparatus of the pendulum variety for readily and easily determining film and the like hardness is adapted to automate all the operations necessarily preceding the commencement of a measurement stage using, in connection therewith, a recording unit or printer to supply the operator with the numerical results of all the measurements without personal manipulation(s). In making a measurement, the necessary time count for passing from amplitude $\alpha$ to amplitude $\beta$ is effected by means of a photo-electric cell. This records the passage of a pendulum arm having a predetermined period during the time that the oscillation amplitude is higher than $\beta$. The involved count gives the measured time necessary for the measurement. The automatic apparatus advantageously reduces error relating to each measurement and increases the number of measurements to be effected on one and the same test film to yield a vastly more reliable mean statistical value. Provision may be made to simultaneously test several films, either by simultaneous of successive mountings of a plurality of films whose hardness is being measured.

66 Claims, 4 Drawing Figures

PENDULUM-TYPE FILM HARDNESS MEASUREMENT TESTER

HISTORY OF THE APPLICATION

The present Application is fully based on and is in complete correspondence with and the equivalent of International Application (under the Patent Cooperation Treaty) No.: PCT/FR78/00042, filed Nov. 28, 1978; which International Application has and claims the priority of French patent application Ser. No. 77.35500, filed Nov. 25, 1977.

BACKGROUND OF THE INVENTION

It is, as is well known, frequently necessary to measure the hardness of a film (for instance of a finger nail varnish film or the film of paint, varnishes, plastic materials, coatings and the like and so forth); and, more generally, of all materials capable of forming skins. To do this, a standardised measure has been developed and defined. This generally uses a pendulum whose oscillating arm rests on the film to be tested. The damping time of the pendulum oscillation is measured, during which time it passes from an angular amplitude $\alpha$ to a lower angular amplitude $\beta$. Provision is made for the pendulum to rest on the film to be tested by means of two half spheres and for the structure of the oscillating pendulum mass to be arranged so that the pendulum should impact on the second one.

In a first embodiment of such a device, widely known in the art and called a "PERSOZ" pendulum, an angle of 12° has been adopted for $\alpha$ and of 4° for $\beta$. In another and second embodiment, generally referred to as "KÖNIG'S pendulum", a value of 6° has been adopted for $\alpha$ and 3° for $\beta$.

In embodiments of the known and mentioned type, a disc of standardised dimensions is positioned on the apparatus carrying the film to be tested. Then the two hemispheres of the pendulum are manually brought to bear on the film. Finally, the pendulum arm is taken to one extreme of its initial oscillating course of and for the value $\alpha$. After that, the pendulum is released; and the time necessary for the pendulum arm to come to oscillate up to an amplitude of value $\beta$ is measured.

It is apparent that there exist many sources of possible errors in the course of the various above-explained measurement stages and steps. In illustration of this, it must be reckoned that:

In the first place, the positioning of the pendulum on the specimen must be effected without any deterioration in the zone of the film to be measured.

Also and secondly, it is necessary to bring the pendulum arm into a position exactly corresponding to angular amplitude $\alpha$. In other words, it is necessary for this procedure to effect a setting in a plane strictly perpendicular to the line joining the two bearing points of the pendulum on the film.

Thirdly, the apparatus must be adjusted so that the plate supporting the film should be strictly horizontal to avoid any slide of the pendulum on the film during the course of the measurement.

Fourthly, from the moment when the pendulum arm is released, it is necessary for the operator to count the time and to turn off or stop the stop-watch (or other time-measuring device) exactly at the moment when the oscillation amplitude becomes equal to the predetermined angle $\beta$. This latter synchronisation is, for all practical purposes, rather difficult to achieve. It also entails a relatively wide scatter of the results obtained for the same measurement. Moreover, the operator is obliged to be permanently present during the whole time of the measurement. And, should the operator have to move the supporting plate for the film in order to do another measurement, it is necessary to effect the handling and then again be present during the whole duration of the subsequent measurement.

PURPOSES AND BENEFITS OF THE INVENTION

In order to advantageously remedy the above-mentioned drawbacks and deficiencies relating to the operation of a hardness test pendulum, it is, according to the invention, proposed to render the measurement sequences relating to such a pendulum automatic and to make it possible to effect a series of successive measurements without any need for the operator to be present when one passes from one measurement to the following measurement. To do this in accordance with the present invention and the discovery on which it is based, the operation of the hardness test pendulum of the known type is made automatic. Likewise and more particularly, so are all the operations necessarily preceeding the commencement of a measurement stage. Moreover, and as further regards the present apparatus, there is therewith connected and in operative association a recording unit, that is to say (and such as), a printer adapted and able so as to supply the operator with the numerical results of all the measurements of a test series effected successively without any intervention by the operator. In the course of one and the same measurement, the necessary time count for passing from amplitude $\alpha$ to amplitude $\beta$ is effected by means of a photoelectric cell. This records the passage of the pendulum arm while the oscillation amplitude is higher than $\beta$. The involved count gives the measured time, since, by virtue of the involved apparatus designed so that the movable parts of the pendulum are determined and embodied in such a way that a predetermined period is calculable for the pendulum. Thus, by rendering the operations of a hardness test pendulum automatic, it is possible, on the one hand, to reduce the error relating to each measurement (such as the scatter of the results) and, on the other hand, to increase the number of measurements to be effected on one and the same film or the like body in order to obtain a mean statistical value which is altogether satisfactory, the standard deviation in the distribution of the results being thereby reduced. Moreover, provision may be made either to dispose several films on the same plate located in different zones of the plate and tested automatically in succession by the pendulum or, to associate with apparatus according to the invention, a plate distributor magazine which allows, when one plate has been subjected to the test, for its removal from the apparatus and its automatic replacement by another plate carrying another film to be tested. It is clear that this automation thus allows the output of a hardness test apparatus to be considerably increased.

FIELD AND OBJECTIVES OF THE INVENTION

This invention, as hereinafter more fully defined and characterized, pertains to and has as its fundamental aim the provision of a novel industrial product comprised of and constituting a much improved apparatus assembly which allows the hardness of a film to be measured; the said apparatus having therein a moving element resting via two bearing points of the film (or like structure) to be tested; the said film being carried by a plate, itself supported by the apparatus; the said moving element being capable of a pendular oscillating motion in a plane perpendicular to the line joining the two aforementioned bearing points; said apparatus comprising, firstly, means allowing the vertical displacement of the moving element in relation to the plate carrying the film; secondly, means allowing the moving element to be brought to one end of its pendular course in a position corresponding to an angular oscillating amplitude of the value of $\alpha$ allowing the moving element to be momentarily held in this position; thirdly, means allowing the displacement of the plate carrying the film to be tested in relation to the moving element when this moving element does not rest (or is not resting) on the film; and fourthly, means allowing the number of pendular oscillations of the moving element to be counted, all of this being characterisable in that the count of the number of pendular oscillations of the moving element is effected and taken only on the oscillations having an amplitude higher than the value of $\beta$, the result of such count being, beneficially, either stored or printed; and further characterizable in that an electronic device allows (after the manual start of a cycle of measurement) to arrange, on one hand, the sequence of bringing the moving element to bear on the plate carrying the film to be tested and, on the other hand, the positioning of the moving element at one end of its course of oscillation in order to release the said moving element to count the number of oscillations up to the angular amplitude $\beta$ and to store or print the results of the count and finally, to raise the moving element again to move the plate carrying the film in relation to the moving element and to start a subsequent test measurement cycle, the sequence of the measurement cycles being stopped when the displacement of the film carrier plate has brought the said plate into a predetermined end position; the furnishment and realization of all of same being amongst the principle objectives of the invention.

BEST MODE OF AND FOR THE INVENTION

In a preferred embodiment of apparatus according to the invention: the bearing points of the moving element are constituted by and made up of spherical caps; the means allowing the moving element to be raised in relation to the film carrier plate in constituted of a stirrup assembly comprising two arms coming on either side of the moving element, the two arms cooperating with side studs carried by the moving element, the stirrup assembly being vertically displaced in relation to the frame of the apparatus by a screw nut or equivalent system; the stirrup assembly is comprised of a zone constituted of a nut which cooperates with a vertical screw driven by an electric motor; the arms of the stirrup assembly being comprised of V-shaped notches which come to cooperate with lateral studs of the moving element; the moving element being constituted, in a known way, of a rectangular frame, one of the small sides of which frame comprise the bearing points of and for the moving element, the other small side carrying a pointer allowing the pendular movements to be recorded; the frame of the apparatus being comprised of a base plate supporting a gallows, the horizontal part of said gallows having and bearing, in its upper portion, the plate carrying the film and traversing the rectangular frame constituting the moving element; the means which allow the moving element to be brought into its initial pendular oscillation position comprising a first carriage capable of horizontal displacement on guides carried by the plate of the frame, the displacement being fitted with a nut which cooperates with a screw made to rotate by an electrical motor carried by the plate of the frame; the displacement of the first carriage, if and when perpendicularly effected coming to the line joining the bearing point of the moving element. The first carriage carries a gallows whose horizontal arm may come into contact with the pointer of the moving element. This gallows is capable of turning around and upon a vertical axis. The moving element is held at the end of the course to which it is brought by the first carriage, this being accomplished by means of an electro-magnet. The plate of the electro-magnet is covered by a magnetic insulating material; the frame of the apparatus carries a count reader constituted of a luminous flux emitter and a photo-electric cell which are respectively arranged on either side of the trajectory of the pointer of the moving element at a point corresponding to the angular amplitude $\beta$ of the pendular oscillation of the moving element. The plate carrying the film is arranged at the upper part of a second carriage with horizontal displacement. The said second carriage is displaced on the upper side of the horizontal arm of the gallows of the frame of the apparatus. The second carriage is driven perpendicularly to the line joining the bearing point of the moving element by means of a screw-nut system. The second carriage carries a nut which cooperates with a screw driven by an electric motor and is carried by the gallows frame. The screws driven by the three electric motors of the apparatus are comprised of and have at their end which is not connected to the corresponding electric motor, a knurled button (or the like). The screws connected to each and every of the three electric motors of the apparatus have individual threads which terminates at a certain distance from the associated end of each given screw to allow a disengagement of the nuts in the case of an accidental over-run of the normal travel. The sliding members connected to the nuts, which cooperate with the three driving screws of the apparatus, cooperate with micro-contacts defining the ends of the normal travel of the said sliding members. The second carriage, by virtue of its horizontal displacement, cooperates by means of stops with a micro-contact carried by the frame in its zone of normal travel. In this, two successive stops corresponding to two successive positions of the second carriage for two successive measurements are effected by the apparatus. In a variant embodiment, the apparatus is associated with a plate distributor magazine which, after a series of measurements have been effected at different points of the film carried by the same plate, allows the change of the plate on the second carriage. The three motors of the apparatus are generally and usually step-wise motors. The count reader is connected to a set of any given "n" quantity of memories capable of storing, each one of the counted results. The counting relating in any given instance to a particular "n" successive measurements is successively stored in the "n" memories of the device. In another variation, the count reader is connected to a printer on which the result of the count is inscribed at the end of each measurement; the reading of the contents of the "n" memories being effected on a digital display therefor in the particularly involved "n" successive operations.

SUMMARY OF THE INVENTION

The present invention and the discovery on which is based relates to an improved apparatus comprising: a moving element resting on two bearing points on the film to be tested; the said film being carried by a plate which plate is itself supported by the apparatus; the said moving element being capable of a pendular oscillating motion in a plane perpendicular to the line joining the said bearing points, with the assembly of said apparatus having therein: firstly, means allowing the moving element to be displaced vertically in relation to the plate carrier of the film; secondly, means allowing the moving element to be brought to one end of its pendular course in a position corresponding to an angular oscillating amplitude of the value of $\alpha$ and allowing the moving element to be momentarily kept in this position; thirdly, means allowing the displacement of the plate carrying the film to be tested in relation to the moving element when such moving element does not rest on the film; and fourthly, means allowing the count of the number of pendular oscillations of the moving element, the same being characterisable in that the count of the number of pendular oscillations of the moving element is effected only on oscillations which have an amplitude higher than the value of $\beta$, with the result of such count being either stored or printed; said apparatus assembly including an electronic device adapted to allow, after a manual starting of a cycle of measurements, effectation of a sequence constituting, on one hand, causation of the moving element to bear on the plate carrier of the film to be tested and, on the other hand, of positioning the moving element at one end of its course of oscillation, to release the said moving element, so as to: count the number of oscillations up to angular amplitude $\beta$ and to store or print the result of the count and finally, to lift the moving element in order to displace the film carrier plate in relation to the moving element and to start a subsequent cycle of measurements, the sequence of measurement cycles being stopped when the displacement of the print carrier plate has brought the said plate into a predetermined end position.

The working assembly and components thereof and therefor plus additional details and other significant specifics of the invention are also set forth in the following.

ILLUSTRATED EXEMPLIFICATION OF THE INVENTION

To render the aims, objectives and purposes of the present invention even more readily understood, an embodiment fully set forth and represented on the accompanying Drawing will hereinafter be more thoroughly described by way and for purposes of showing a merely illustrative and non-restrictive illustrative exemplification of the invention.

PARTICULARIZED DESCRIPTION OF THE INVENTION

Figure 1:
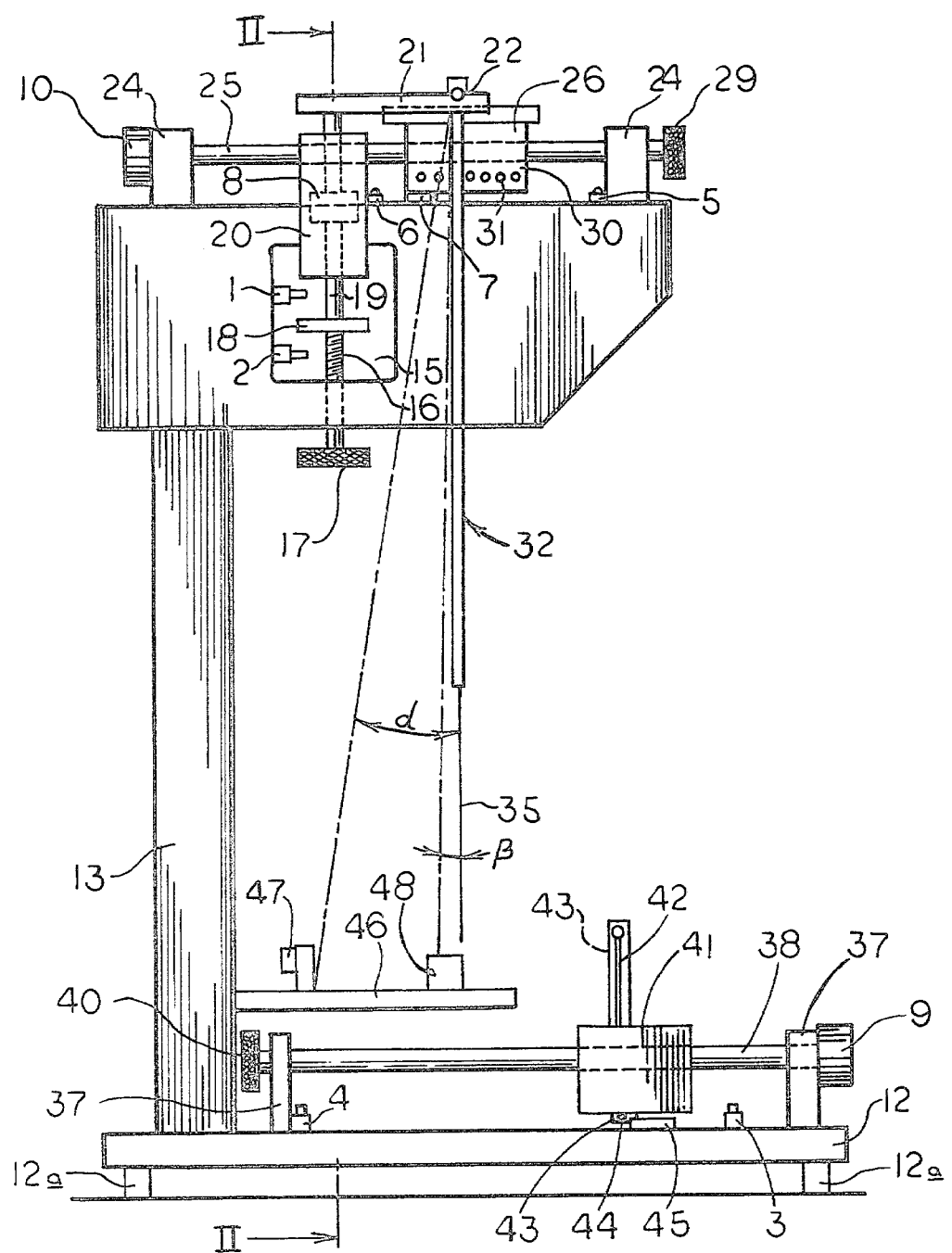
FIG. 1 is a view showing an elevation of an apparatus in accordance with the invention involving a "PEROZ" type of pendulum apparatus.
Figure 2:
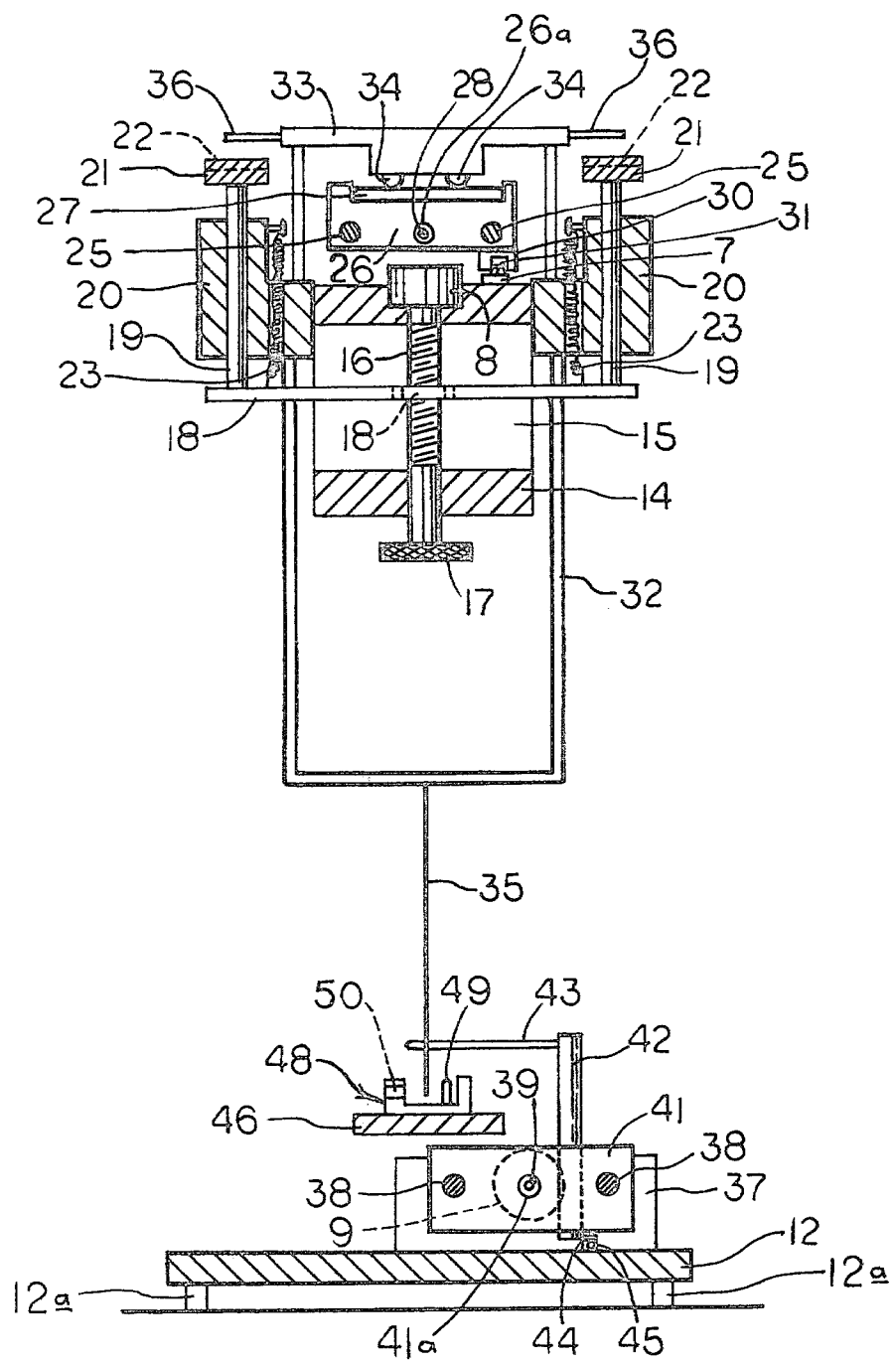
FIG. 2 is a view, in vertical cross-section taken along the Line II—II in FIG. 1, showing a particular aspect of the apparatus.
Figure 3:
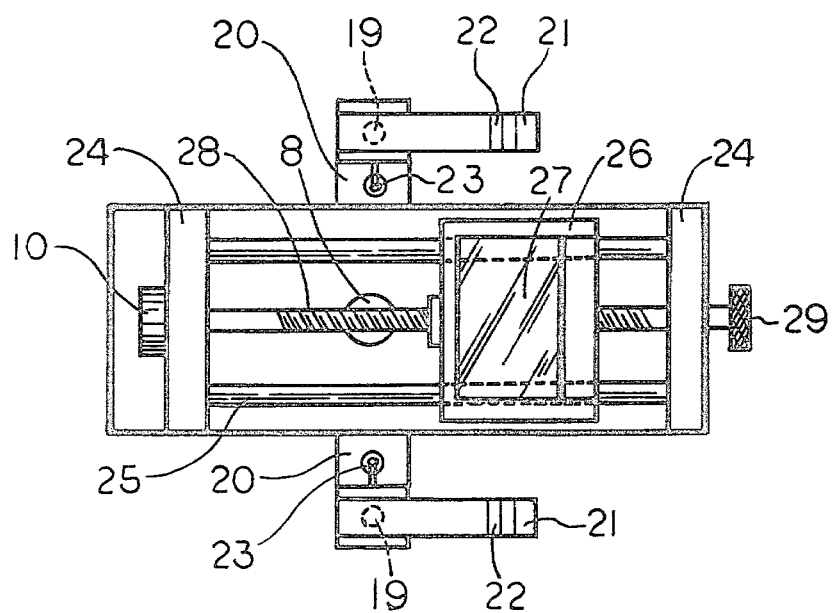
FIG. 3 is a plan view showing the horizontal arm of the gallows frame.

According to the present invention and with associated reference to the several FIGURES and views of the accompanying Drawing, it will be seen that the frame of the apparatus has been generally designated, as a whole, by reference numeral 11. Frame 11 comprises a base plate 12 which rests on the supporting table and which supports a gallows constituted by a tubular vertical element 13 and a horizontal arm 14. The arm 14 is transversely comprised of a cut-out 15, this being traversed by a vertical screw 16. One end of the screw 16 is provided with a knurled button 17. Its other end is driven by an electric motor 8. The electric motor 8 is positioned in a housing cut out on the upper face of the horizontal arm 14 of the frame.

With screw 16, there cooperates a plate 18 which traverses cut-out 15 from end-to-end and which carries in its central zone a nut 18a by means of which the plate 18 may be displaced vertically by the rotation of screw 16. The vertical movement of plate 18 is guided by two rods, each identified by reference numeral 19, which are fixed to the plate 18 and which slide in a guide 20 affixed to arm 14 of the frame 11. The two rods 19 are arranged vertically on either side of the horizontal arm 14. Each of the rods 19 carry on their uppermost parts an arm 21 which is horizontally arranged above the upper side of arm 14.

The entirety of elements 18, 19, and 21 constitutes a stirrup which is vertically moveable. The two arms 21 comprise and each are components of a V-shaped notch 22; the two notches 22 being aligned along a straight line which is perpendicular to the vertical center plane of arm 14.

A helical spring 23 is arranged vertically on either side of arm 14 between a locking stud fixed to guide 20 and plate 18. The thread of screw 16 does not extend up to the lower extremity of this screw. Thus, if nut 18a happens to come disengaged from this thread, it is nonetheless maintained against the start of the said thread by the action of two springs 23. Moreover, springs 23 are designed so that their vertical traction substantially balances the weight of stirrup 18, 19, and 21.

The upper side of arm 14 carries two cross heads 24. These are perpendicular to the center vertical plane of arm 14 and are arranged and disposed near the two ends of the said arm 14. Between the cross heads 24, there extend two parallel guide rods 25. These actually constitute slides which are associated with a carriage 26 that is capable of supporting a plate 27 on its upper part. Plate 27 is a glass plate of standard dimensions. On this plate is arranged the film (or other substrate) whose hardness is intended to be measured. For example, this may be a polymer film.

The horizontal position of plate 27 is controlled by means of a spirit level. The level is generally placed on the upper side of carriage 26, and is adjustable by means of three jack screws, each identified by reference numeral 12a, fixed on the lower side of base plate 12. In its central zone, carriage 26 comprises a nut 26a. This nut cooperates with a screw 28 which is horizontally arranged at least about an equal distance from the two guide rods 25 in the central vertical plane of arm 14.

Screw 28 is supported at its two ends by the two cross heads 24. It is connected at one of its ends to a knurled button 29. At its other end, screw 28 is connected to a step-wise electric motor 10. Carriage 26 is fitted along one of its edges parallel to guide rod 25 on its lower side with a U shaped profile 30. In the two sides of the U, bores are arranged to allow for the positioning of two needles 31 which connect the two sides of the U section. These needles 31 constitute the ends which cooperate with a micro-contact 7 which is placed on the upper surface of arm 14.

To make and effect a hardness measurement on the film (or the like) borne by the upper side of plate 27, there is thereon placed a moving element which bears thereupon. This moving element is constituted of a rectangular frame, traversed by arm 14 of the frame. The moving element is designated generally by reference numeral 32. The rectangular frame of element 32 comprises two short horizontal sides plus two long vertical sides. The short horizontal side 33, which constitutes the upper arm of the frame, carries two hemispheres 34 on its lower side, which constitute the bearing points of the moving element 32 on the film (or the like) to be tested. The short horizontal arm is usually at the lower part of the frame. It supports, in its central zone, a needle 35 which is parallel to the two long sides of the frame of moving element 32. Moving element 32 is capable of being brought into pendular motion around the defined axis by the two bearing points 34. The embodiment of moving element 32 is such that a pendulum thus-constituted beats seconds. The dimensions adopted for the moving element and for plate 27 satisfy the relative standards defined for hardness tests. On either side of the horizontal arm 33 of moving element 32, there are arranged pins 36. These lie in the extension of the center line of arm 33 as well as in the same vertical plane as notches 22.

Base plate 12 of frame 11 carries two cross heads 27, each and both of which are parallel with cross heads 24. Cross heads 37 are interconnected between and by means of the two guide rods 38 which are parallel to guide rods 25. At the same distance from guide rods 38, there is arranged a screw 39. Screw 39 is supported at its extremities by the cross heads 37. Screw 39 is driven at one of its extremities by an electric step-wise motor 9. At its other end, screw 39 has provided thereon a knurled knob 40. On guide rods 38, there may slide a carriage 41. This is comprised of a nut 41a cooperating with screw 39. Carriage 41 carries a gallows constituted by a vertical rod 42 and a horizontal arm 43. This gallows is capable of turning around the vertical axis of rod 42 so as to produce the pivoting of the horizontal arm 43 around the said axis. The control of the pivoting of gallows 42, 43 is obtained by means of a pin 44 which is fixed to the lower part of rod 42. The pin 44 cooperates with a cam 45 carried by base plate 12. As is observable in FIG. 1 of the accompanying Drawing, a displacement of carriage 41 towards the right (as may be reckoned in the view of FIG. 1) entails, by the action of cam 45 on pin 44, a rotation of rod 42 to bring arm 43 to be parallel to the plane of moving element 32. Movement in the opposite direction entails and brings into action the opposite rotation of gallows 42, 43 under the urging of a spring.

Tubular element 13 carries a support plate 46. This plate is parallel to base plate 12 and is situated above the base plate 12 at a level sufficient for carriage 41 to be displaced below plate 46. Plate 46 is symmetrical in relation to the vertical center plane of the apparatus. The vertical rod 42 is, in the course of motion of the involved apparatus, shifted laterally in relation to plate 46. The end of horizontal arm 43 is disposed above plate 46 when carriage 41 is in the left hand half (as can be seen in FIG. 1) of its horizontal displacement travel. Thus, this arm comes into contact with needle 35 of moving element 32 and is able to carry needle 35 towards the left (see FIG. 1) during a corresponding displacement of carriage 41. Needle 35 of moving element 32 may thus be brought into contact with the plate of an electromagnet 47 carried by plate 46. The plate of electromagnet 47 is covered with a layer of the material known under the commercial designation "TEFLON" (a fluorohydrocarbon polymer available from E. I. DuPONT DeNEMOURS & CO., Inc.). The fact that the plate of electromagnet 47 has been covered by means of a magnetic insulating material makes it possible to be certain that any phenomenon of magnetic remanence is avoided at the time the pendular movement is started and in the few following oscillations. The position of electromagnet 47 corresponds to the initial amplitude of the pendular movement of moving element 32. Thus it directly relates to an angle c according to whether one passes from one standardised method to another.

Plate 46 also carries a count reader, designated generally by reference numeral 48. The count reader 48 is constituted of a U-shaped section. The pendular movement of needle 35 is effected between the two sides of the U parallel to the same two sides. At the bottom of the section which rests on plate 46, there is arranged a lamp 49. This lamp emits a light in the direction of the photo-electric cell 50 carried by one of the sides of the U-shaped section constituting section 48. The plane of oscillation of needle 35 is disposed between lamp 49 and cell 50. Because of this, cell 50 supplies a pulse on each passage of the needle in its front. The position of count reader 48 on plate 46 is arranged so that cell 50 supplies a pulse at the moment when needle 35 passes in its pendular movement to an angular position $\beta$ in relation to the vertical. If the amplitude of the pendular movement of moving element 32 happens to be less than angle $\beta$, cell 50 no longer supplies any pulse. The position on plate 46 of reader 48 is adjustable so that the value of angle $\beta$ may be varied according to the standard used for the measurement.

The illustrated apparatus, moreover, is provided with micro-contracts which allow for the ends of the normal travel of the movable elements comprising it to be detected in motion. The ends of the travel of plate 18 are detected by micro-contacts 1 and 2, respectively, for the upper and lower ends. The ends of the travel of the first carriage, (i.e., carriage 41) are detected by the micro-contacts 3 and 4, respectively, for the right and left ends as shown in FIG. 1. The sequence control of the moving members and of the time count for each measurement is effected by means of an electronic device hereinafter more fully described.

It is apparent that, if the electronic device has a disruption or breakdown, apparatus in accordance with the present invention can, nevertheless, be used manually by manipulating screws 16, 28, and 39 respectively by means of the knurled buttons 17, 29 and 40.

It is further observable that the movements of the moving members of the apparatus are ensured by electric motors 8, 9, 10. These, as mentioned, are step-wise motors comprising four supply phases which make it possible to avoid any inertia capable of entailing errors of positioning and ensure great accuracy in the automation of the operation of the apparatus.

Obtaining a film hardness measurement by means of the described apparatus is effected as follows:

(i) stirrup assembly 18, 19, 21 is elevated into the high position to raise moving element 32 by supporting pins 36 in notches 22;

(ii) carriage 26 is then displaced towards the right (as is evident in FIG. 1) until micro-contact 5 is made to operate; and then (iii) on carriage 26, plate 27 is disposed, the upper side of which is covered with the film to be tested. The apparatus is then ready for the commencement of a measurement (or measurements) cycle.

Stirrup assembly 18, 19, 21 is lowered to cause moving element 32 to rest on plate 27. Carriage 41 is displaced towards the left, per the depiction of FIG. 1. Such displacement causes arm 43 to come into contact with needle 35 and, thereupon, to push the said needle in the direction of electromagnet 47 which is thereby energised. When needle 35 is held against electromagnet 47, carriage 41 is made to move in the opposite direction until the carriage movement causes micro-contact 3 to work. In the course of this movement, arm 43 pivots by 90 and frees the trajectory of needle 35.

The supply of electromagnet 47 is then cut. When this happens, the moving element 32 commences its pendular movement, with the associated number of oscillations being counted by reader 48. When the amplitude of the oscillation declines below $\beta$, the count is stopped; and stirrup 18, 19, 21 is then caused to rise which ensures the elevation of the moving element. After this, carriage 26 is caused to be displaced towards the left from the right, as depicted in FIG. 1. This displacement is effected and continued until the needle 31 comes into contact and cooperation with micro-contact 7. At this point and moment, carriage 26 stops. A new cycle of measurement then recommences.

The succession of measurements continues until micro-contact 7 no longer cooperates with any needle 31, in which case, the displacement of carriage 26 causes the latter to actuate micro-contact 6. This then allows the succession of the effected measurements to be terminated. The results of the various measurements have by this time been successively stored for rereading, as desired, on a numerical display.

In the here-described embodiment, four memories have been provided to allow for four successive measurements to be stored. To do this, provision is made to position three needles 31. In the case where the device associated with the apparatus comprises a printer, it suffices to direct the result of the counts to the printer without any storage. In this way, the number of successive measurements on the same plate may be considerably increased without in any way increasing the complexity of the associated electronic device. In such cases, the number of needles 31 must also be increased because their total number must be equal to $(n-1)$ to effect "n" successive measurements.

As is perceivable in the Drawing, provision is made for the plate 27 to be slightly shifted in relation to the axis of the moving element so that a 180° turn of plate 27 in its own major plane makes it possible to effect a new series of measurements on the same film being test measured without impacting again on the points where the measurements have been effected before the turning of the plate.

Figure 4:
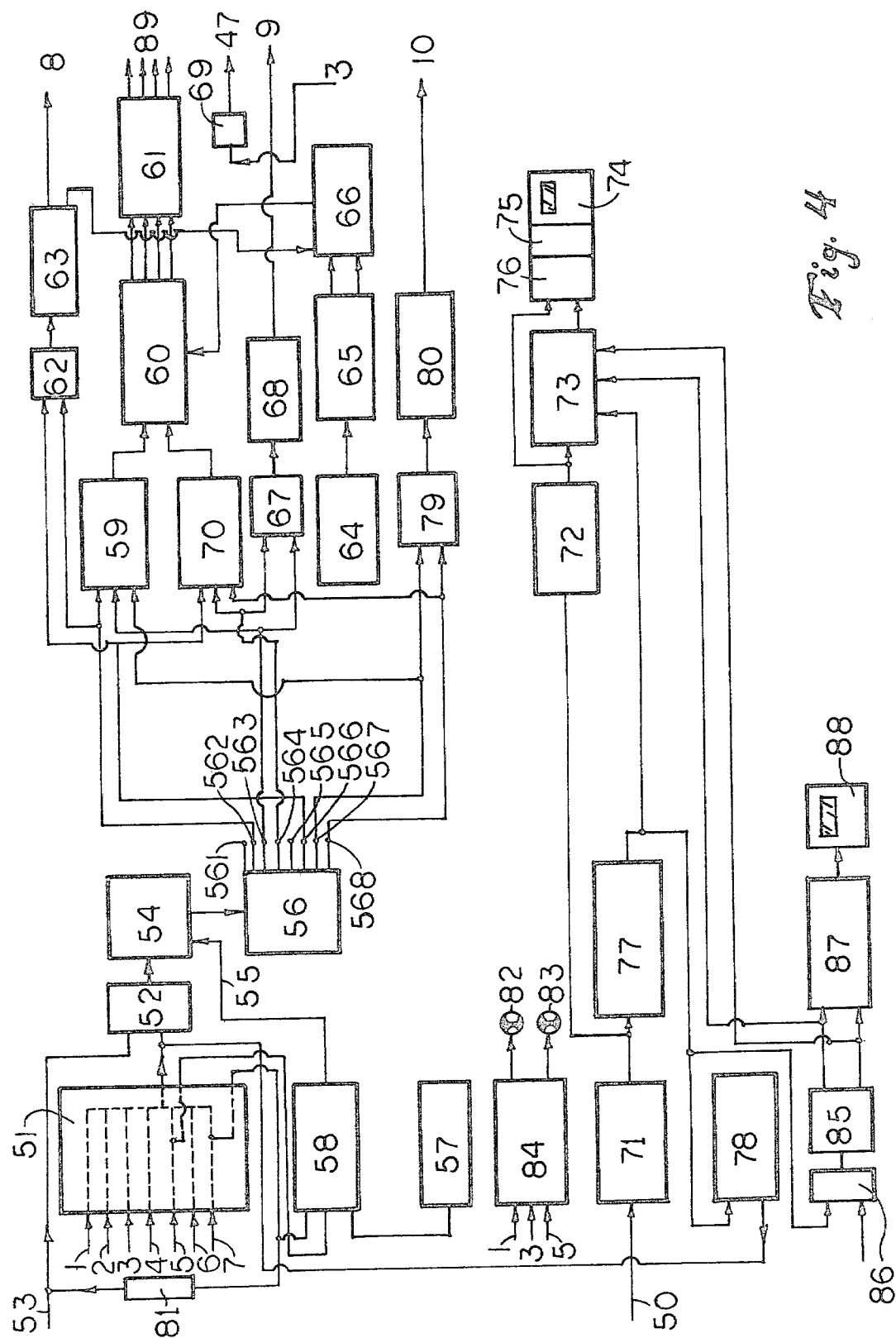
FIG. 4 is a view, in block diagrammatic representation, demonstrating a suitable electronic device associated with the apparatus of FIG. 1, which device allows the sequence of the various movements of a series of successive measurements effected at various points of the film carried by the same plate to be controlled automatically.

The electronic device which allows the above-described apparatus to be automatically controlled is schematically represented in FIG. 4 of the accompanying Drawing. The signals emanating from micro-contacts 1, 2, 3, 4, 5, 6, and 7 are sent to a differentiator 51 which supplies a pulse at zero ("0") level at the time of the rising front of the signal as the same is supplied by one of the micro-contacts. At the beginning of a measurement cycle, micro-contacts 1, 3, and 5 are closed. Therefore, at this point, they supply a signal at level "1", due to the fact that plate 18 is in the high position and carriages 41 and 26 are at the right hand end of their travel as is shown in FIG. 1.

The output of differentiator 51 is sent to a "Nand" (meaning—NO AND—) gate 52 which receives, on its other input, the pulse contingently supplied by the circuit closer which allows a succession of measurements in and with use of the apparatus to be started according to the manipulated of the operator. This pulse is received via line 53. Gate 52 energises a binary counter 54, the return to zero of which has been designated by 55. The binary counter 54 counts on three bits and feeds a decoder 56. Decoder 56 comprises 8 outputs corresponding to the eight binary numbers capable of being counted by counter 54. The eight outputs are designated by reference numerals 561 and 568. They correspond respectively to numerical FIGS. 1 to 8 after decoding. Outputs 561 and 565 are not branched. At the start of a sequence (i.e., when the circuit of the apparatus is switched on), a return to zero ("0") is ensured by a switch on device 57 which energises an "AND" gate 58 and resets counter 54 to zero via line 55. It follows that when the circuit is switched on, output 561 of decoder 56 is at zero while all the other outputs are at level "1".

At the time when a pulse is sent via line 53 for the start of a succession of measurements, gate 52 supplies a pulse at level "1" because the input fed by differentiator 51 is at level "1". The binary counter 54 counts a unit so that output 562 of the decoder is placed at "0" level, all the other outputs being at level "1". Output 562 is connected to an "OR" gate 59 which also receives outputs 563 and 567. Gate 59 then supplies a pulse to a shift register 60 which controls the supply of the four phases of step-wise motors 8, 9, and 10 via element 63, the energisation of motor 8. Thus, one obtains the displacement towards the bottom of stirrup assembly 18, 19, 21 and the bearing of moving element 32 on the film to be tested.

A time piece 64 supplies pulses at an "F" frequency. These pulses are sent to a frequency divider 65, which supplies pulses at frequency F/2 and at frequency F/4 at the same time. These two frequencies are supplied to a decoder 66. Decoder 66 feeds the shift register 60 either with frequency F/2 or with frequency F/4, according to the indications it receives from device 63. When device 63 orders the energisation of motor 8, it also sends a pulse to decoder 66 which then supplies frequency F/4. In any given case where device 63 does not supply any signal, decoder 66 supplies frequency F/2 to register 60. From this, it necessarily follows that when motor 8 is energised, the phases of motor 8 receive pulses at a low frequency so that motor 8 turns slowly. On the other hand, at the moment when motors 9 and 10 will be energised, the supply frequency of the phases will be high. This allows obtention of rapid movements for motors 9 and 10. Thus, a slow bearing of moving element 32 on the film with accompanying rapid displacement of carriages 41 and 26 is ensured.

When device 63 has ordered or commanded motor 8 to be supplied with current, moving element 32 is made to bear on the film to be tested. Plate 18 then also comes to actuate micro-contact 2. Differentiator 51 then gives a pulse at level "0" and gate 52 gives a pulse at level "1". Counter 54 increases by one unit and decoder 56 places output 563 at level "0"; all other outputs remaining at level "1". It follows that the "OR" gate 59 still has one of its inlets at level "0" which ensures via register 60 and transistors 61 that the four phases of motors 8, 9 and 10 are supplied. But the current supply for motor 8 is no longer assured because gate 562 has passed to level "1", whereas the power supply of motor 9 is then ensured because gate 563 feeds the "OR" gate 67 whose output actuates device 68 which starts the energisation of motor 9. Thus the displacement of carriage 41 is obtained towards the left, as shown in the representation of FIG. 1. This displacement takes place until carriage 41 comes to actuate micro-contact 4. In this movement of carriage 41, needle 35 is brought on to electromagnet 47 whose energisation is ensured by placing contact 3 at level "0" by means of the power gate 69.

When needle 35 is held by electro-magnet 47, carriage 41 arrives at the end of its travel and actuates micro-contact 4. This then sends a pulse at level "0" to differentiator 51 and therefor a pulse to counter 54. Output 564 passes to level "0", while all the other outputs of decoder 56 are at level "1". Output 564 feeds an input to an "OR" gate 70 whose output controls the shift register 60. The power supply of the four phases of motors 8, 9, and 10 is thereby controlled; yet the feed via gate 70 produces a shift in the opposite direction of the supply via gate 59. In this way, an order of register 60 via gate 70 produces an actuation of motors 8, 9, and 10 in the opposite direction to the actuation obtained when register 60 receives its instruction from gate 59. Output 564 also feeds an input of "OR" gate 67 and, through the intermediary of device 68, the energisation of motor 9. From this, it follows that the rotation of motor 9 is thus ordered in the opposite direction to that of the preceding command which returns carriage 41 towards the right, as illustrated in FIG. 1 of the accompanying drawing.

When carriage 41 arrives at the end of its travel, it actuates micro-contact 3. This causes a pulse to be sent to differentiator 51 and therefore increases the count of counter 54 by one unit. Output 565 of decoder 56 passes to level "0" whereas all the other outputs are at level "1". At this point, line 67/68 no longer ensures the electric power supply of motor 9 resulting in stoppage of carriage 41. From this it also follows that device 69 no longer ensures the energisation of electro-magnet 47 which produces the start of the pendular oscillation movement of moving element 32.

Cell 50 sends a signal on each passage of needle 35. This signal enters a pulse-shaping circuit 71 which transmits a count pulse after every second cell pulse, the count pulses being sent to a 4 bits binary counter 72. Counter 72 feeds a group of four memories 73, each comprising four bits. Simultaneously, it also feeds a display unit 74 connected to a decoder 75 and a demultiplexer 76. Pulse-shaping circuit 71 also feeds a timing circuit 77. Circuit 77 emits a signal when a time space greater than the period of the moving element (for example, 1.5 seconds) has passed without any pulse being emitted by circuit 71. Since the pendulum constituted by moving element 21 beats every second, it is clear that circuit 71 supplies a pulse per second while needle 35 passes in front of cell 50. When the amplitude of the pendulum declines below angle $\beta$, needle 35 no longer passes in front of the cell and, therefore, the timing circuit 77 supplies a signal which is sent, on the one hand, to the memory store block 73 which ensures that the indication supplied at this moment by counter 72 is registered in one of the memories of block 73 and, on the other hand, to a differentiator 78, which gives a pulse at the moment of the descending front of the pulse emitted by timing circuit 77.

The pulse supplied by differentiator 78 is thus sent at the end of the count pulse which is produced by timing circuit 77 to gate 52. This pulse has "0" level. It therefore produces an increase of the count of counter 54 and the setting at level "0" of output 566 of decoder 56, whereas all the other outputs are brought to level "1". Output 566 is connected to an inlet of the "OR" gate 70; consequently producing supplies for the four phases of motors 8, 9, 10 in direction corresponding to the opposite direction of the initial movement produced by an actuation due to gate 59. Simultaneously, output 566 actuates an input of "OR" gate 62 and, as a consequence, the energisation of motor 8 via device 63. Thus, an upward return movement of stirrup assembly 18, 19, 21 is produced upon raising of moving element 32. Since pins 36 come to be positioned within notches 22, the pendular movement of element 32 is stopped instantly in any such elevating action.

The rise of stirrup assembly 18, 19, 21 occurs until micro-contact 1 is actuated. At this moment, the input of the differentiator 51 (connected to the micro-contact 1) passes from level "0" to level "1". This produces an increase in the count of counter 54 by one unit. It also occasions the passing to level "0" of output 567 of decoder 56 with all the other outputs passing to level "1".

Output 567 feeds one of the inputs of an "OR" gate 79 which actuates the energisation of motor 10 by means of device 80. Moreover, output 567 feeds an input of the "OR" gate 59 which actuates the current supplies for the four phases of motors 8, 9, 10. It will therefore be seen that one thus obtains a movement of carriage 26 from the right towards the left as taken by viewing of FIG. 1. In the course of this displacement, one of needles 31 comes to actuate micro-contact 7. The corresponding input of differentiator 51 then passes to level "1". Differentiator 51 supplies, at the time the level of input connected to micro-contact 7 changes, a pulse which is sent to one of the inputs of the "AND" gate 58 to thus actuate the resetting to zero of counter 54. The resetting to zero simultaneously and immediately entails a zero setting of the level of gate 561 of decoder 56 and the setting to level "1" of all the other outputs. This action, as is apparent, does not then incur any movement for any of the motors of the apparatus. The pulse emitted by differentiator 51 at the time the level of the input connected to micro-contact 7 changes is also sent by means of a retardation circuit 81 to the input line 53 by which the operator had started the sequence of measurements. It is thus evident that, in this way, a new cycle of measurement is recommended after carriage 26 has been displaced.

This sequence of operations continues until the displacement of carriage 26 no longer causes any needle 31 to come into contact with micro-contact 7. In this case, the displacement of carriage 26 is produced until microcontact 6 is actuated. A luminous indicator (not shown) is then energized and illuminated; the said indicator being actuated by micro-contact 6 connected to a rocker (also not shown). The input of differentiator 51, which corresponds to micro-contact 6, then passes from level "0" to level "1"; and binary counter 54 is increased by one unit. Decoder 56 causes output 568 to pass to level "0", whereas the other outputs are set at level "1". Output 568 is connected to one of the inputs of the "OR" gate 79 and to one of the inputs of "OR" gate 70. The "OR" gate 79 orders the energisation of motor 10 through the intermediary of device 80. The feed of "OR" gate 70 actuates through the intermediary of register 60 the supply for the four phases of motors 8, 9, 10. From this, motor 10 is correspondingly actuated in a direction of rotation opposite of that which had been produced for all the preceding commands which had passed through the intermediary of gate 59.

Thus, a return movement back of carriage 26 is produced from the left towards the right, as is discernable from FIG. 1. During this movement, output 568 (which is at level "0") inhibits, by way of an "AND" gate, the signals issued from the micro-contact. This movement continues until carriage 26 causes micro-contact 5 to be actuated. At this moment, the change in level of the corresponding input of differentiator 51 entails the supply of a pulse to the input of gate 58 and consequently, a resetting to zero of the binary counter 54. In this way there is possibilitated a return to the initial state. This, in other words, is the state wherein the entirety of the electronic circuits are in the same condition as they were just prior to the moment when the operator had sent a starting pulse on line 53.

The electronic device connected to the apparatus according to the invention also comprises indicators 82, 83. These allow the operator to be informed regarding the state of the apparatus before the despatch of a starting signal on line 53. Indicators 82, 83 are connected to a circuit 84 whose inputs are connected to micro-contacts 1, 3 and 5. As previously indicated, micro-contacts 1, 3, and 5 must supply a signal at level "1" at the moment when the operator is to commence a sequence of measurements. If the three inputs are at level "1", indicator 82 is lit up and indicator 83 is extinguished. Obviously, if one of the three inputs is not at level "1", indicator 83 is lit up and indicator 82 is extinguished.

As also previously indicated, memory block 73 comprises four memories of four bits each. Storage in the memory is ensured after each measurement. Thus, with such a memory block, the results of four successive measurements may be stored.

Taking account of the preceding explanations, the possibility of storing four successive memories supposes that three needles 31 are arranged on carriage 26. When the sequence of measurements has been terminated, it is necessary to be able to re-read the memory contents. The content of the last memory is displayed on display unit 74. But, it is necessary to have the facility of displaying on display unit 74 the contents of each of the four memories of block 73. To do this, a cycles counter 85 is made available in order to receive, by way of an "OR" gate 86, the pulses of the end of count emitted by timer 77. One of the inlets of the "OR" gate 86 also receives the pulses which the operator may emit from a push button. Counter 85 is connected to a decoder 87 which feeds a four digit display unit 88. Moreover, counter 85 feeds the memory block 73 by sending to the block the address indications which allow one of the memories of the memory block to be selected and to display on display unit 74 the contents of this memory. It will thus be seen that, on one hand, the cycles counter 85 allows the storage of successive measurements in the different memories of block 73 and that, on the other hand, it allows the content of one of the memories of the block to be displayed on display unit 74. The operator may thus, when a sequence of measurements has been terminated, successively re-read the contents of all the memories of block 73.

It shall be fully understood that the above-particularly-described embodiment in no way is restrictive; and the same may give rise to any desirable modifications without thereby departing from the scope of the invention; in particular: the means allowing the vertical displacement of the moving element; the means allowing the said moving element to be brought to one end of its course; and the means allowing the displacement of the plate which carries the film to be tested, all or any portion of which may be constituted by mechanisms and appliances other than the screw nut system (for example, rack or wheel mechanisms) and simple motors for driving with direct current arrangements, in place of step-wise motors, and so forth.

In keeping with the immediate foregoing, it is apparent that many changes and modifications can readily be made and adapted in embodiments in accordance with the present invention without substantially departing from its apparent and intended spirit and scope, all in pursuance and accordance with same as it is set forth and defined in the hereto appended claims.

What is claimed is:

1. Apparatus for measuring the hardness of film and the like comprising:
   a moving element resting on two bearing points on the film to be tested;
   a plate supported by the apparatus for carrying said film;
   the said moving element being capable of a pendular oscillating motion in a plane that is perpendicular to the line joining the said bearing points, with
   the assembly of said apparatus being further characterized by therein having:
   a first means for vertically displacing the said moving element in relation to the plate carrier of the film;
   a second means for bringing said moving element to one end of its pendular course in a position that corresponds to an angular oscillating amplitude of the value of $\alpha$ thereby allowing the moving element to be momentarily kept in this position;
   a third means for displacing the plate carrying the film to be tested in relation to said moving element when such moving element is not resting on the film; and
   a fourth means for counting the number of pendular oscillations of the moving element, said fourth means being further characterizable in that
   the count thereby made of the number of pendular oscillations of said moving element is effected only on oscillations which have an amplitude which is higher than the value of $\beta$ with the result of such count being either stored or printed;
   said apparatus assembly also including and being comprised of:
   an electronic device means operable after manual starting of a cycle of measurements for effectuation of a sequence which is constituted, on one hand, of causation of said moving element to bear on said plate carrier of the film to be tested and, on the other hand, positioning of the moving element at one end of its course of oscillation, whereby and whereupon said moving element is released so as to then:

initially count the number of oscillations up to angular amplitude β and to store or print the result of such count; and thereafter and finally, left said moving element in order to displace the said film carrier plate in relation to the said moving element and thereupon to start a subsequent cycle of measurements, the sequence of measurement cycles being stopped when the displacement of the print carrier plate has brought the said plate into a predetermined end position.

2. Apparatus according to that of claim 1, wherein the bearing points of the moving element are constituted of spherical caps.

3. Apparatus according to claim 2, wherein:

the means allowing the lifting of the moving element in relation to the film plate carrier are constituted by a stirrup assembly comprising two arms extending on either side of the moving element;

the two arms cooperating with lateral studs are carried by the moving element; and the stirrup assembly is vertically displaced in relation to the frame of the apparatus by a screw-nut system.

4. Apparatus according to that of claim 3, wherein the stirrup assembly is comprised of a zone constituted by a nut which cooperates with a vertical screw driven by an electric motor.

5. Apparatus according to claim 2, wherein:

the moving element is constituted by a rectangular frame, one of the short sides of which comprises the bearing points of said moving element; while the other small side of said frame carries a needle adapted to allow the pendular movement to be identified;

the said rectangular frame being traversed in its horizontal part by a gallows which is supported by a base plate and which constitutes the frame of the apparatus, the said horizontal part of the gallows supporting on its upper side, the film carrier plate.

6. Apparatus according to that of claim 5, wherein the said second carriage is driven perpendicularly to the line which joins the bearing points of the moving element by means of a screw-nut system.

7. Apparatus according to that of claim 6, wherein the said second carriage carries a nut which cooperates with a screw driven by an electric motor and is carried by the gallows of the frame.

8. Apparatus according to claim 1, wherein:

the means allowing the lifting of the moving element in relation to the film plate carrier are constituted by a stirrup assembly comprising two arms extending on either side of the moving element;

the two arms cooperating with lateral studs are carried by the moving element; and the stirrup assembly is vertically displaced in relation to the frame of the apparatus by a screw-nut system.

9. Apparatus according to that of claim 8, wherein the stirrup assembly is comprised of a zone constituted by a nut which cooperates with a vertical screw driven by an electric motor.

10. Apparatus according to claim 9 and being further characterised in that the screws driven by the three electric motors of the apparatus comprise at their end which is not connected to the corresponding electric motor, a knurled button.

11. Apparatus according to claim 9 and being further characterised in that the screws associated with each one of the electric motors of the apparatus have a thread which stops at a certain distance from the termination thereof to allow a disengagement of the nuts in the case of an accidental over-run of the normal travel.

12. Apparatus according to claim 9 and being further characterised in that the moving members associated with the nuts which cooperate with the three driving screws are adapted to cooperate with micro-contacts defining the terminating ends of the normal travel of the said moving members.

13. Apparatus according to claim 9 and being further characterised in that the three drive motors are stepwise motors.

14. Apparatus according to claim 9, wherein the arms of the stirrup assembly comprise V-shaped notches which are adapted to cooperate with the side studs of the moving element.

15. Apparatus according to claim 9, wherein:

the moving element is constituted by a rectangular frame, one of the short sides of which comprises the bearing points of said moving element; while the other small side of said frame carries a needle adapted to allow the pendular movement to be identified;

the said rectangular frame being traversed in its horizontal part by a gallows which is supported by a base plate and which constitutes the frame of the apparatus;

the said horizontal part of the gallows supporting on its upper side, the film carrier plate.

16. Apparatus according to that of claim 15, wherein the said second carriage is driven perpendicularly to the line which joins the bearing points of the moving element by means of a screw-nut system.

17. Apparatus according to that of claim 16, wherein the said second carriage carries a nut which cooperates with a screw driven by an electric motor and is carried by the gallows of the frame.

18. Apparatus according to claim 8, wherein the arms of the stirrup assembly comprise V-shaped notches which are adapted to cooperate with the side studs of the moving element.

19. Apparatus according to claim 18, wherein:

the moving element is constituted by a rectangular frame, one of the short sides of which comprises the bearing points of said moving element; while the other small side of said frame carries a needle adapted to allow the pendular movement to be identified;

the said rectangular frame being traversed in its horizontal part by a gallows which is supported by a base plate and which constitutes the frame of the apparatus, the said horizontal part of the gallows supporting on its upper side, the film carrier plate.

20. Apparatus according to that of claim 19, wherein the said second carriage is driven perpendicularly to the line which joins the bearing points of the moving element by means of a screw-nut system.

21. Apparatus according to that of claim 20, wherein the said second carriage carries a nut which cooperates with a screw driven by an electric motor and is carried by the gallows of the frame.

22. Apparatus according to claim 5, wherein:
the moving element is constituted by a rectangular frame, one of the short sides of which comprises the bearing points of said moving element; while
the other small side of said frame carries a needle adapted to allow the pendular movement to be identified;
the said rectangular frame being traversed in its horizontal part by a gallows which is supported by a base plate and which constitutes the frame of the apparatus,
the said horizontal part of the gallows supporting on its upper side, the film carrier plate.

23. Apparatus according to that of claim 22, wherein the said second carriage is driven perpendicularly to the line which joins the bearing points of the moving element by means of a screw-nut system.

24. Apparatus according to that of claim 23, wherein the said second carriage carries a nut which cooperates with a screw driven by an electric motor and is carried by the gallows of the frame.

25. Apparatus according to claim 1, wherein:
the moving element is constituted by a rectangular frame, one of the short sides of which comprises the bearing points of the said moving element; while
the other small side of said frame carries a needle adapted to allow the pendular movement to be identified;
the said rectangular frame being traversed in its horizontal part by a gallows which is supported by a base plate and which constitutes the frame of the apparatus,
the said horizontal part of the gallows supporting on its upper side, the film carrier plate.

26. Apparatus according to claim 25, wherein:
the said film carrier plate is arranged on the upper side of a second carriage with horizontal displacement; and
the said second carriage being displaced on the upper side of the horizontal arm of the gallows of the frame of the apparatus.

27. Apparatus according to that of claim 26, wherein:
the second carriage means of and with its horizontal displacement cooperates by stops with a microcontact carried by the frame in its zone of normal travel; and wherein there are
two successive stops corresponding to two successive positionings of the second carriage for two successive measurements effected by the apparatus.

28. Apparatus according to that of claim 26, wherein said assembly combination is connected to a plate dispenser magazine adapted, after a series of measurements has been effected at different points of the film carried by the same plate, to allow the plate to be changed on the second carriage. point which corresponds to angular amplitude β of the pendular oscillation of the moving element.

29. Apparatus according to that of claim 26, wherein the said second carriage is driven perpendicularly to the line which joins the bearing points of the moving element by means of a screw-nut system.

30. Apparatus according to that of claim 29, wherein the said second carriage carries a nut which cooperates with a screw driven by an electric motor and is carried by the gallows of the frame.

31. Apparatus according to any one of claims 5, 15, 19 or 22, inclusive, wherein:
the second carriage means of and with its horizontal displacement cooperates by stops with a microcontact carried by the frame in its zone of normal travel; and wherein there are
two successive stops corresponding to two successive positionings of the second carriage for two successive measurement effected by the apparatus.

32. Apparatus according to any one of claims 5, 15, 19 or 22, inclusive, wherein said assembly combination is connected to a plate dispenser magazine adapted, after a series of measurements has been effected at different points of the film carried by the same plate, to allow the plate to be changed on the second carriage.

33. Apparatus according to any one of claims 6, 23, 16 or 20, inclusive, and being further characterised in that the screws driven by the three electric motors of the apparatus comprise at their end which is not connected to the corresponding electric motor, a knurled button.

34. Apparatus according to any one of claims 6, 23, 16, or 20, inclusive, and being further characterised in that the screws associated with each one of the electric motors of the apparatus have a thread which stops at a certain distance from the termination thereof to allow a disengagement of the nuts in the case of an accidental over-run of the normal travel.

35. Apparatus according to any one of claims 6, 23, 16 or 20, inclusive, and being further characterised in that the moving members associated with the nuts which cooperate with the three driving screws are adapted to cooperate with microcontacts defining the terminating ends of the normal travel of the said moving members.

36. Apparatus according to any one of claims 6, 16, 20 or 23, inclusive, and being further characterised in that the three drive motors are step-wise motors.

37. Apparatus according to any one of claim 25, 5, 22, 15 or 19 wherein the frame of the apparatus carries a count reader constituted by a luminous flux emitter and a photo-electric cell arranged on either side of the trajectory of the needle of the moving element at a point which corresponds to angular amplitude β of the pendular oscillation of the moving element.

38. Apparatus according to that of claim 37, wherein the reader of the count is connected to a printer on which the result of the count is inscribed at the end of each measurement.

39. Apparatus according to that of claim 37, wherein:
the said count reader is connected to a set of "n" memories capable of each storing a count result;
the count referring to "n" successive measurements being stored successively in the "n" memories of the device; and in which
"n" is an integer greater than 1.

40. Apparatus according to that of claim 39, wherein the reading of the contents of the "n" memories is effected on a digital display in "n" successive operations.

41. Apparatus according to any one of claims 1, 2, 3, 8, 4, 5, 22, 15 or 19, inclusive, wherein:
the means allowing the moving element to be brought into its initial position of pendular oscillation is comprised of:
a first carriage capable of displacement by way of horizontal translation on guides carried by the base plate of the frame;
said displacement being controlled by a screw-nut system.

42. Apparatus according to claim 41, and being further characterised in that said first carriage carries a gallows whose horizontal arm may come into contact with the needle of the moving element, the said gallows being capable of turning around a vertical axis.

43. Apparatus according to claim 41, and being further characterised in that the moving element is held at the end of its travel where it is brought by the first carriage by means of an electromagnet.

44. Apparatus according to claim 43, wherein the plate of the electromagnet is covered with a magnetic insulating material.

45. Apparatus according to claim 41 and being further characterised in that the displacement of the first carriage is effected perpendicularly to the line joining the bearing points of the moving element.

46. Apparatus according to claim 45 and being further characterised in that the moving element is held at the end of its travel where it is brought by the first carriage by means of an electromagnet.

47. Apparatus according to that of claim 46, wherein the plate of the electromagnet is covered with a magnetic insulating material.

48. Apparatus according to claim 45 and being further characterised in that said first carriage carries a gallows whose horizontal arm may come into contact with the needle of the moving element, the said gallows being capable of turning around a vertical axis.

49. Apparatus according to claim 48 and being further characterised in that the moving element is held at the end of its travel where it is brought by the first carriage by means of an electromagnet.

50. Apparatus according to that of claim 49, wherein the plate of the electromagnet is covered with a magnetic insulating material.

51. Apparatus according to that of claim 41 and being further characterised in that the first carriage is provided with a nut which cooperates with a screw drive for rotation by an electric motor carried by a fixed frame.

52. Apparatus according to claim 51 and being further characterised in that the screws driven by the three electric motors of the apparatus comprise at their end which is not connected to the corresponding electric motor, a knurled button.

53. Apparatus according to claim 51 and being further characterised in that the screws associated with each one of the electric motors of the apparatus have a thread which stops at a certain distance from the termination thereof to allow a disengagement of the nuts in the case of an accidental over-run of the normal travel.

54. Apparatus according to claim 51 and being further characterised in that the moving members associated with the nuts which cooperate with the three driving screws are adapted to cooperate with micro-contacts defining the terminating ends of the normal travel of the said moving members.

55. Apparatus according to claim 51 and being further characterised in that the three drive motors are step-wise motors.

56. Apparatus according to claim 51 and being further characterised in that the moving element is held at the end of its travel where it is brought by the first carriage by means of an electromagnet.

57. Apparatus according to that of claim 56, wherein the plate of the electromagnet is covered with a magnetic insulating material.

58. Apparatus according to claim 51 and being further characterised in that said first carriage carries a gallows whose horizontal arm may come into contact with the needle of the moving element, the said gallows being capable of turning around a vertical axis.

59. Apparatus according to claim 58 and being further characterised in that the moving element is held at the end of its travel where it is brought by the first carriage by means of an electromagnet.

60. Apparatus according to that of claim 59, wherein the plate of the electromagnet is covered with a magnetic insulating material.

61. Apparatus according to claim 51 and being further characterized in that the displacement of the first carriage is effected perpendicularly to the line joining the bearing points of the moving element.

62. Apparatus according to claim 61 and being further characterised in that the moving element is held at the end of its travel where it is brought by the first carriage by means of an electromagnet.

63. Apparatus according to that of claim 62, wherein the plate of the electromagnet is covered with a magnetic insulating material.

64. Apparatus according to claim 61 and being further characterised in that said first carriage carries a gallows whose horizontal arm may come into contact with the needle of the moving element, the said gallows being capable of turning around a vertical axis.

65. Apparatus according to claim 64 and being further characterised in that the moving element is held at the end of its travel where it is brought by the first carriage by means of an electromagnet.

66. Apparatus according to that of claim 65, wherein the plate of the electromagnet is covered with a magnetic insulating material.

* * * * *